US012318064B2

(12) United States Patent
Komp et al.

(10) Patent No.: US 12,318,064 B2
(45) Date of Patent: Jun. 3, 2025

(54) THORACIC IMAGING, DISTANCE MEASURING, SURGICAL AWARENESS, AND NOTIFICATION SYSTEM AND METHOD

(71) Applicant: Covidien LP, Mansfield, MA (US)

(72) Inventors: John W. Komp, Dillon, CO (US); Joe D. Sartor, Longmont, CO (US); Irena Cantrall, Boulder, CO (US)

(73) Assignee: Covidien LP, Mansfield, MA (US)

( * ) Notice: Subject to any disclaimer, the term of this patent is extended or adjusted under 35 U.S.C. 154(b) by 157 days.

(21) Appl. No.: 18/130,361

(22) Filed: Apr. 3, 2023

(65) Prior Publication Data

US 2023/0233059 A1 Jul. 27, 2023

Related U.S. Application Data

(62) Division of application No. 16/682,566, filed on Nov. 13, 2019, now Pat. No. 11,617,493.

(Continued)

(51) Int. Cl.
*A61B 1/00* (2006.01)
*A61B 1/04* (2006.01)
(Continued)

(52) U.S. Cl.
CPC .... *A61B 1/000094* (2022.02); *A61B 1/00194* (2022.02); *A61B 1/046* (2022.02);
(Continued)

(58) Field of Classification Search
CPC . A61B 1/00; A61B 1/000094; A61B 1/00194; A61B 1/046; A61B 17/04;
(Continued)

(56) References Cited

U.S. PATENT DOCUMENTS 3,928,925 A 12/1975 Gay
5,057,494 A 10/1991 Sheffield
(Continued)

FOREIGN PATENT DOCUMENTS

BR 0013237 A 7/2003
BR 0116004 A 6/2004
(Continued)

OTHER PUBLICATIONS

First Office Action issued in Chinese Patent Application No. 201911278464.8 dated Jan. 26, 2024 with English translation.
(Continued)

*Primary Examiner* — Vi X Nguyen
(74) *Attorney, Agent, or Firm* — Weber Rosselli & Cannon LLP

(57) ABSTRACT

A method for enhanced surgical navigation, and a system performing the method and displaying graphical user interfaces associated with the method. A 3D spatial map of a surgical site is generated using a 3D endoscope including a camera source and an IR scan source. The method includes detecting a needle tip protruding from an anatomy and determining a needle protrusion distance corresponding to a distance between the needle tip and a surface of the anatomy using the 3D spatial map. A position of a surgical tool in the 3D spatial map is detected and a determination is made by the system indicative of whether the needle protrusion distance is sufficient for grasping by the surgical tool. A warning is generated when it is determined that the needle protrusion distance is not sufficient for grasping by the surgical tool.

12 Claims, 8 Drawing Sheets

Related U.S. Application Data

(60) Provisional application No. 62/782,683, filed on Dec. 20, 2018, provisional application No. 62/779,229, filed on Dec. 13, 2018, provisional application No. 62/779,242, filed on Dec. 13, 2018.

(51) Int. Cl.
*A61B 1/06* (2006.01)
*A61B 17/04* (2006.01)
*A61B 34/20* (2016.01)
*A61B 17/00* (2006.01)

(52) U.S. Cl.
CPC ............. *A61B 1/06* (2013.01); *A61B 1/0605* (2022.02); *A61B 1/0655* (2022.02); *A61B 17/0482* (2013.01); *A61B 17/0491* (2013.01); *A61B 34/20* (2016.02); *A61B 2017/00128* (2013.01); *A61B 2017/00809* (2013.01); *A61B 2034/2051* (2016.02); *A61B 2034/2055* (2016.02); *A61B 2034/2057* (2016.02); *A61B 2034/2065* (2016.02)

(58) Field of Classification Search
CPC ............ A61B 17/0491; A61B 17/0482; A61B 2017/00809
See application file for complete search history.

(56) References Cited

U.S. PATENT DOCUMENTS

| | | | |
|---|---|---|---|
| 5,321,113 A | 6/1994 | Cooper et al. | |
| 5,687,737 A | 11/1997 | Branham et al. | |
| 6,003,517 A | 12/1999 | Sheffield et al. | |
| 7,474,407 B2 | 1/2009 | Gutin | |
| 7,538,859 B2 | 5/2009 | Tearney et al. | |
| 7,559,895 B2 | 7/2009 | Stetten et al. | |
| 7,756,305 B2 | 7/2010 | Price | |
| 7,857,756 B2 | 12/2010 | Warren et al. | |
| 7,949,385 B2 | 5/2011 | Khamene et al. | |
| 7,952,718 B2 | 5/2011 | Li et al. | |
| 8,335,359 B2 | 12/2012 | Fidrich et al. | |
| 8,335,557 B2 | 12/2012 | Maschke | |
| 8,382,662 B2 | 2/2013 | Soper et al. | |
| 8,384,909 B2 | 2/2013 | Yun et al. | |
| 8,460,195 B2 | 6/2013 | Courtney et al. | |
| 8,494,794 B2 | 7/2013 | Dutta et al. | |
| 8,706,184 B2 | 4/2014 | Mohr et al. | |
| 8,784,321 B2 | 7/2014 | Courtney et al. | |
| 8,827,934 B2 | 9/2014 | Chopra et al. | |
| 8,983,580 B2 | 3/2015 | Boppart et al. | |
| 9,375,268 B2 | 6/2016 | Long | |
| 9,398,936 B2 | 7/2016 | Razzaque et al. | |
| 9,554,774 B2 | 1/2017 | Moore et al. | |
| 9,861,338 B2 | 1/2018 | Kanade et al. | |
| 9,918,659 B2 | 3/2018 | Chopra et al. | |
| 10,004,558 B2 | 6/2018 | Long et al. | |
| 10,194,897 B2 | 2/2019 | Cedro et al. | |
| 10,350,009 B2 | 7/2019 | Panescu et al. | |
| 10,368,054 B2 | 7/2019 | Panescu et al. | |
| 10,373,719 B2 | 8/2019 | Soper et al. | |
| 10,376,178 B2 | 8/2019 | Chopra | |
| 10,391,277 B2 | 8/2019 | Rahimian et al. | |
| 10,405,753 B2 | 9/2019 | Sorger | |
| 10,478,162 B2 | 11/2019 | Barbagli et al. | |
| 10,480,926 B2 | 11/2019 | Froggatt et al. | |
| 10,524,866 B2 | 1/2020 | Srinivasan et al. | |
| 10,555,788 B2 | 2/2020 | Panescu et al. | |
| 10,569,071 B2 | 2/2020 | Harris et al. | |
| 10,603,106 B2 | 3/2020 | Weide et al. | |
| 10,610,306 B2 | 4/2020 | Chopra | |
| 10,638,953 B2 | 5/2020 | Duindam et al. | |
| 10,639,114 B2 | 5/2020 | Schuh et al. | |
| 10,674,970 B2 | 6/2020 | Averbuch et al. | |
| 10,682,070 B2 | 6/2020 | Duindam | |
| 10,702,137 B2 | 7/2020 | Deyanov | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 11,172,184 B2 | 11/2021 | Komp et al. | |
| 2002/0147462 A1 | 10/2002 | Mair et al. | |
| 2003/0013972 A1 | 1/2003 | Makin | |
| 2004/0120981 A1 | 6/2004 | Nathan | |
| 2004/0210105 A1 | 10/2004 | Hale et al. | |
| 2006/0084860 A1 | 4/2006 | Geiger et al. | |
| 2008/0045938 A1 | 2/2008 | Weide et al. | |
| 2009/0262979 A1* | 10/2009 | Markowitz | A61B 5/061 382/128 |
| 2010/0217117 A1 | 8/2010 | Glossop et al. | |
| 2012/0209069 A1 | 8/2012 | Popovic et al. | |
| 2013/0018255 A1 | 1/2013 | Kitamura et al. | |
| 2013/0303945 A1 | 11/2013 | Blumenkranz et al. | |
| 2014/0035798 A1 | 2/2014 | Kawada et al. | |
| 2014/0163359 A1 | 6/2014 | Sholev et al. | |
| 2014/0243596 A1 | 8/2014 | Yoon et al. | |
| 2014/0336461 A1* | 11/2014 | Reiter | A61B 1/00193 600/111 |
| 2015/0148690 A1 | 5/2015 | Chopra et al. | |
| 2015/0235373 A1 | 8/2015 | Kato et al. | |
| 2015/0238276 A1 | 8/2015 | Atarot et al. | |
| 2015/0265368 A1 | 9/2015 | Chopra et al. | |
| 2016/0081653 A1 | 3/2016 | Masuda et al. | |
| 2016/0151119 A1 | 6/2016 | Michel et al. | |
| 2016/0157939 A1 | 6/2016 | Larkin et al. | |
| 2016/0183841 A1 | 6/2016 | Duindam et al. | |
| 2016/0192860 A1 | 7/2016 | Allenby et al. | |
| 2016/0287344 A1 | 10/2016 | Donhowe et al. | |
| 2017/0035380 A1 | 2/2017 | Barak et al. | |
| 2017/0112571 A1 | 4/2017 | Thiel et al. | |
| 2017/0112576 A1 | 4/2017 | Coste-Maniere et al. | |
| 2017/0172662 A1* | 6/2017 | Panescu | A61B 34/35 |
| 2017/0209071 A1 | 7/2017 | Zhao et al. | |
| 2017/0265952 A1 | 9/2017 | Donhowe et al. | |
| 2017/0280970 A1 | 10/2017 | Sartor et al. | |
| 2017/0311844 A1 | 11/2017 | Zhao et al. | |
| 2017/0319165 A1 | 11/2017 | Averbuch | |
| 2018/0078318 A1 | 3/2018 | Barbagli et al. | |
| 2018/0144092 A1 | 5/2018 | Flitsch et al. | |
| 2018/0153621 A1 | 6/2018 | Duindam et al. | |
| 2018/0200001 A1 | 7/2018 | Erbe | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263527 A1 | 9/2018 | Kitamura | |
| 2018/0263706 A1 | 9/2018 | Averbuch | |
| 2018/0279852 A1 | 10/2018 | Rafii-Tari et al. | |
| 2018/0310831 A1 | 11/2018 | Cheng et al. | |
| 2018/0325419 A1 | 11/2018 | Zhao et al. | |
| 2019/0000559 A1 | 1/2019 | Berman et al. | |
| 2019/0000560 A1 | 1/2019 | Berman et al. | |
| 2019/0008413 A1 | 1/2019 | Duindam et al. | |
| 2019/0038365 A1 | 2/2019 | Soper et al. | |
| 2019/0065209 A1 | 2/2019 | Mishra et al. | |
| 2019/0110839 A1 | 4/2019 | Rafii-Tari et al. | |
| 2019/0175062 A1 | 6/2019 | Rafii-Tari et al. | |
| 2019/0175799 A1 | 6/2019 | Hsu et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0269818 A1 | 9/2019 | Dhanaraj et al. | |

(56) References Cited

U.S. PATENT DOCUMENTS

| | | |
|---|---|---|
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0020127 A1 | 1/2020 | Hirakawa |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054398 A1 | 2/2020 | Kovtun et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0107886 A1 | 4/2020 | Govari et al. |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |
| 2021/0220078 A1 | 7/2021 | Godhani et al. |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CN | 103565484 A | 2/2014 |
| CN | 103796597 A | 5/2014 |
| CN | 107198567 A | 9/2017 |
| CN | 108289598 A | 7/2018 |
| CZ | 1644519 A | 12/2008 |
| CZ | 486540 B1 | 9/2016 |
| CZ | 2709512 B6 | 8/2017 |
| CZ | 2884879 B1 | 1/2020 |
| EP | 1644519 B1 | 12/2008 |
| EP | 2141497 A1 | 1/2010 |
| EP | 3225151 A1 | 10/2017 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| JP | 2008018172 A | 1/2008 |
| MX | PA03005028 A | 1/2004 |
| MX | PA03000137 A | 9/2004 |
| MX | PA03006204 A | 9/2004 |
| MX | 225663 B | 1/2005 |
| MX | 226292 B | 2/2005 |
| MX | PA03010507 A | 7/2005 |
| MX | PA05011725 A | 5/2006 |
| MX | 06011286 | 3/2007 |
| MX | PA06011286 A | 3/2007 |
| MX | 246862 B | 6/2007 |
| MX | 2007006441 A | 8/2007 |
| MX | 265247 B | 3/2009 |
| MX | 284569 B | 3/2011 |

OTHER PUBLICATIONS

Communication pursuant to Article 94(3) EPC issued in European Patent Application No. 19215514.1 dated Dec. 4, 2023.
Notification to Grant Patent Right for Invention issued in Chinese Patent Application No. 201911278581.4 dated Jan. 26, 2024 with English translation.
European Search Report issued in European Patent Application No. EP 19215517 dated Apr. 14, 2020, 9 pages.
Non-Final Office Action issued in U.S. Appl. No. 16/682,351 dated Mar. 28, 2022.
Notice of Allowance issued in U.S. Appl. No. 17/521,714 dated Apr. 7, 2023.
Office Action issued in U.S. Appl. No. 16/682,801 dated Nov. 30, 2020, 25 pages.

* cited by examiner

THORACIC IMAGING, DISTANCE MEASURING, SURGICAL AWARENESS, AND NOTIFICATION SYSTEM AND METHOD

CROSS-REFERENCE TO RELATED APPLICATION

This application is a divisional of U.S. patent application Ser. No. 16/682,566, filed on Nov. 13, 2019, which claims the benefit of U.S. Provisional Patent Application Ser. No. 62/779,242, filed on Dec. 13, 2018, and is related to, and claims the benefit of, U.S. Provisional Patent Application Ser. No. 62/779,229, filed on Dec. 13, 2018 and U.S. Provisional Patent Application Ser. No. 62/782,683, filed on Dec. 20, 2018, the entire contents of each of which being incorporated by reference herein.

BACKGROUND

Technical Field

The disclosure relates to surgical systems, and more particularly, to systems and methods of performing endoscopic thoracic imaging and treatment.

Description of Related Art

Current monocular optical devices (e.g. endoscope, bronchoscope, colonoscope) used for viewing surgical fields during minimally invasive surgery (e.g. laparoscopy) and visual diagnostic procedures (e.g. colonoscopy, bronchoscopy) provide limited reference information on the absolute position of surgical tools and anatomical features because the image has no depth of field. To compensate, surgeons may advance the surgical tool until it comes in contact with a feature or another tool. This leads to inefficient motion and the potential for perforation of critical anatomical structures. Binocular (also known as stereoscopic) optical devices provide limited depth of field affording the surgeon visual information on the distance between items within the optical device's field of view. The accuracy of distance information is limited based on the amount of parallax provided by the optical paths, determined by the distance between the optical paths, and the amount of overlap between the two optical paths.

SUMMARY

In an aspect of the disclosure, a method for enhanced surgical navigation is provided. The method includes generating a 3D spatial map of a surgical site using a 3D endoscope including a camera source and an IR scan source. The method additionally includes detecting whether a needle tip of a needle is protruding from an anatomy in the 3D spatial map, determining a needle protrusion distance by measuring a distance between the needle tip and a surface of the anatomy using the 3D spatial map when the needle tip is protruding from the anatomy, and detecting a position of a surgical tool in the 3D spatial map. Additionally, the method includes determining whether the needle protrusion distance is sufficient for grasping by the surgical tool based on the detected position of the surgical tool. A warning is generated when it is determined that the needle protrusion distance is not sufficient for grasping by the surgical tool based on the detected position of the surgical tool. Additionally, in an aspect, the method includes projecting a needle exit location based on a current orientation of the needle when the needle tip is not protruding from the anatomy.

In an aspect, the method further includes displaying an indication representing a best position on the needle tip to grasp. Additionally, or alternatively, the method further includes displaying an indication representing a best position on the anatomy for a subsequent stitch based on at least one of a distance from an edge of the anatomy, a thickness of the anatomy, a distance from a previous stitch, or any combinations thereof.

In an aspect, generating the warning includes notifying a user to further protrude the needle or to adjust the position of the surgical tool. Additionally, or alternatively, the method includes detecting a type of surgical tool in the 3D spatial map. Determining whether the needle protrusion distance is sufficient for grasping by the surgical tool may be based on the detected position of the surgical tool and the detected type of surgical tool.

In an aspect, the method further includes displaying a value representing the needle protrusion distance. Generating the warning may include modifying the display of the value representing the needle protrusion distance. The generated warning may include at least one of an audible notification or a visual notification.

In an aspect, the 3D spatial map includes a matrix of equidistant data points representing fixed points in a current view of the surgical site and a value of a data point represents an existence of an object at the data point in space. Determining the needle protrusion distance may include calculating a difference between coordinates of two data points in the matrix or following a contour of a surface between two data points in the matrix and calculating a distance along the contour.

In an aspect, the method further includes determining whether a portion of the surgical tool is hidden by an object in the surgical site. Using data from the 3D spatial map, a hidden portion of the surgical tool may be displayed when it is determined that a portion of the surgical tool is hidden by an object in the surgical site.

Additionally, or alternatively, the method may include detecting properties of the anatomy, determining whether the position of the surgical tool is optimal for grasping the anatomy based on the detected properties of the anatomy, and generating a warning when it is determined that the position of the surgical tool is not optimal for grasping the anatomy. An indication of a position on the anatomy for grasping the anatomy may be displayed when it is determined that the position of the surgical tool is optimal for grasping the anatomy.

In yet another aspect of the disclosure, a system for enhanced surgical navigation is provided. The system includes a 3D endoscope including a camera source and an IR source and a computing device operably coupled to the 3D endoscope. Either the 3D endoscope or the computing device is configured to generate a 3D spatial map of the surgical site. The computing device is configured to detect whether a needle tip of a needle is protruding from an anatomy in the 3D spatial map, determine a needle protrusion distance by measuring a distance between the needle tip and a surface of the anatomy using the 3D spatial map when the needle tip is protruding from the anatomy, and detect a position of a surgical tool in the 3D spatial map. A warning is generated when it is determined that the needle protrusion distance is not sufficient for grasping by the surgical tool based on the detected position of the surgical tool. Additionally, in an aspect, the computing device is configured to project a needle exit location based on a current orientation of the needle when the needle tip is not protruding from the anatomy and to display an indication representing a best position on the needle tip to grasp.

In an aspect, the computing device is further configured to display the 3D spatial map of the surgical site on a graphical user interface. Additionally, or alternatively, the computing device is further configured to display an indication representing a best position on the anatomy for a subsequent stitch based on at least one of a distance from an edge of the anatomy, a thickness of the anatomy, a distance from a previous stitch, or any combinations thereof.

The generated warning includes at least one of an audible notification or a visual notification. In an aspect, the computing device is further configured to detect a type of surgical tool in the 3D spatial map and determine whether the needle protrusion distance is sufficient for grasping by the surgical tool based on the detected position of the surgical tool and the detected type of surgical tool. Additionally, or alternatively, the computing device is further configured to display a value representing the needle protrusion distance and modify the display of the value when it is determined that the needle protrusion distance is not sufficient for grasping by the surgical tool based on the detected position of the surgical tool.

The 3D spatial map may include a matrix of equidistant data points representing fixed points in a current view of the surgical site and a value of a data point represents an existence of an object at the data point in space, and the computing device may be configured to determine the needle protrusion distance by calculating a difference between coordinates of two data points in the matrix or following a contour of a surface between two data points in the matrix and calculating a distance along the contour. In an aspect, the computing device is further configured to determine whether a portion of the surgical tool is hidden by an object in the surgical site; and use data from the three-dimensional map to display a hidden portion of the surgical tool in phantom when it is determined that a portion of the surgical tool is hidden by an object in the surgical site.

In yet another aspect of the disclosure, a non-transitory computer-readable storage medium is provided. The non-transitory computer-readable storage medium is encoded with a program that, when executed by a processor, causes the processor to generate a 3D spatial map of a surgical site, detect whether a needle tip of a needle is protruding from an anatomy in the 3D spatial map, determine a needle protrusion distance by measuring a distance between the needle tip and a surface of the anatomy using the 3D spatial map when the needle tip is protruding from the anatomy, and detect a position of a surgical tool in the 3D spatial map. A warning is generated when the needle protrusion distance is not sufficient for grasping by the surgical tool based on the detected position of the surgical tool.

In an aspect, the 3D spatial map includes a matrix of equidistant data points representing fixed points in a current view of the surgical site and a value of a data point represents an existence of an object at the data point in space, and the processor is configured to determine the needle protrusion distance by calculating a difference between coordinates of two data points in the matrix or following a contour of a surface between two data points in the matrix and calculating a distance along the contour.

BRIEF DESCRIPTION OF THE DRAWINGS

Various aspects and features of the disclosure are described hereinbelow with references to the drawings, wherein.

DETAILED DESCRIPTION

Figure 1:
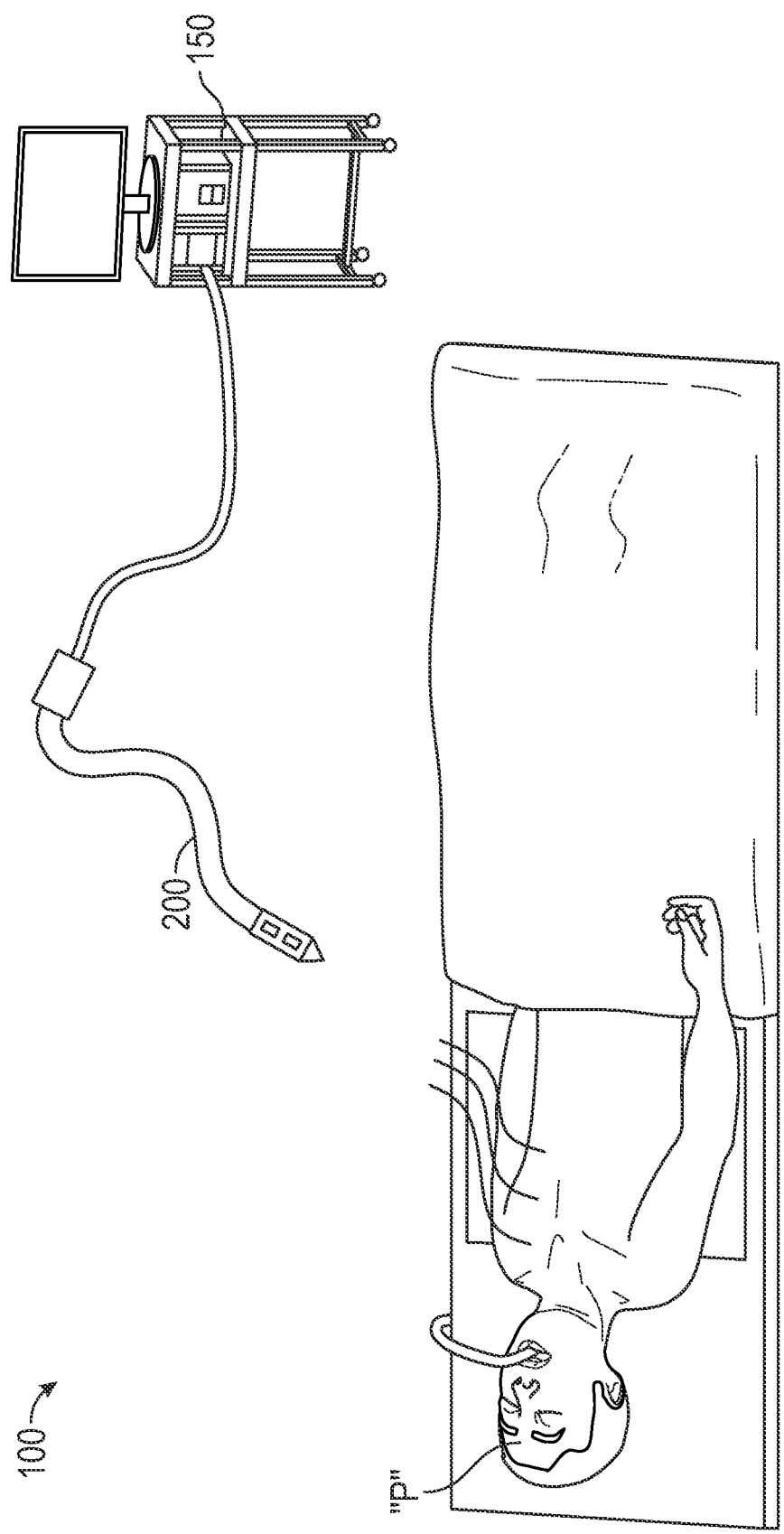
FIG. 1 is a schematic illustration of a surgical imaging system including a 3D endoscope and a computing device for generating a 3D spatial map in accordance with the disclosure.

The disclosure is directed to derivation and display of distance references between objects both within the current optical view and previously viewed objects that may no longer be in view. For example, when suturing the surgeon needs to know when the suture needle end is sufficiently exposed, within the functional grasp area of a tool, and that sufficient needle will be grasped by the tool such that it does not slip out once grasped. As described in greater detail below, for exposure, the positional system can detect the needle end and provide the surgeon with information on how far the needle tip has protruded from the anatomy such that a tool can grasp the needle. When the tool attempts to grasp the needle, the positional system informs the user when the needle and the grasp tool are oriented such that a solid grasp will be possible. The position system further informs the user regarding the location or position on the needle to best grab based on the bite size of the next stitch or the surgical tool used.

As described in greater detail below, the system can demark special locations on tissues to best achieve spatial indications such as suture space and distance from edge. For example, in hysterectomy, the most reliable closure comes with sutures placed 1 cm apart and 1 cm from the edge of the vaginal cuff. This spacing and distance is often missed due to the magnification of endoscopes resulting in closure failure as well documented in robotic procedures. Further, as robots move toward autonomy this ability to layout spatial parameters like suture spacing enables autonomic actions by the robot. A similar example exists in Ventral hernia where it is even more difficult to identify and execute the correct suture depth and spacing as the view plane of the abdominal wall is acute from the camera centerline being the camera is placed laterally from a typical midline hernia and compounded from the orientation being from up, not down.

Further, and as described in greater detail below, tools that enclose a portion of anatomy such as staplers, manipulators, and bi-polar ablation tools require the surgeon to see both sides of the anatomy before enclosure to assure that the tool has been properly deployed and only the intended anatomy will be captured while not causing injury to any critical structure. Using the spatial mapping system and enhanced surgical navigation system described below, the portion of the tool that is hidden by the anatomy can be shown in the surgical display. This might be of the form of a shadow or other symbology that does not distract the surgeon's primary view. The surgeon could also rotate the current display such that the currently hidden parts come into view providing the ability to look around the corner. The display can highlight any critical structures in the general area as a reminder.

Additionally, there are times when the orientation of the surgical tool is suboptimal during minimally invasive surgery. This can create torque on the tool causing a misalignment of the tool jaws. The spatial mapping system and enhanced surgical navigation system described below detects the misalignment and notifies the surgeon to correct the problem before an incomplete or incorrect surgical step occurs (e.g. resulting in a jammed stapler or incomplete ablation). The system can also recognize the size of the anatomy grasped and compare it to the size of the tool to verify there is a match. This prevents issues such as using too short of a staple line requiring using a new larger stapler and increasing the size of the anatomy impacted.

One aspect of the disclosure is directed to a 3D endoscope and systems that support organ matching to preoperative images, for example images of a lung, other anatomy or anatomical features within a surgical site. The 3D endoscope can provide both visual imaging and also surface mapping and is used to generate a 3D spatial map, either by the 3D endoscope or by another component of the system such as a computing device. The computing device utilizes the 3D spatial map to provide enhanced navigational guidance including distance measurements, warnings or other notifications when a surgical device is placed near or is approaching a portion of the anatomy within the surgical site and suggested grasping or contact points on either the anatomy or an object within the surgical site such as a needle.

In accordance with the disclosure, as will be described in greater detail below, the 3D endoscope (also referred to herein as the "endoscope") includes a structured light (or laser) scanner. As can be appreciated, the structured light scanner may employ infrared light so as to avoid interference from visible light sources, although it is contemplated that the structured light scanner may emit light in the visible spectrum, depending upon the tissue being scanned during the procedure. The structured light source includes a known position relative to a camera and permits the calculation of the exact location of the intersection between the light ray from the structured light source and the camera. This information can be scanned as single points, lines, or arrays to create topologic maps of surfaces. In embodiments, the structured light source is that of an LED or LED infrared laser that is dispersed into a scan pattern (line, mesh, or dots), buy rotating mirror, beam splitter, or diffraction grating. In one non-limiting embodiment, the structured light source may be a LED laser having collimated light. The laser scanner will enable visualization systems to achieve accurate surface maps of the anatomy (e.g., the lung) needed in order to match preoperative computed images to the operative image delivered to the endoscopic camera.

In particular applications, the endoscope position will also be tracked by intraoperative instrument tracking systems for example electromagnetic navigation systems. The locational information obtained by the intraoperative instrument tracking system aids in simplifying the algorithms needed to produce large-scale spatial surface maps from segmental sized scans taken from an endoscope. Further, this immediate intraoperative guidance of the optical image location to the surface map and preoperative computed images provides even greater clarity of location and orientation of the endoscope.

In certain embodiments, the 3D endoscope is positionable by a robotic system. The robotic system provides precise six axis orientation of the endoscope in a similar manner to the navigation systems but benefited by active positioning as well as locational knowledge of the endoscope within the patient. As can be appreciated, the robot may be utilized to autonomously move the endoscope to complete scans of larger areas or whole organs.

In one embodiment, the endoscope includes a visual-light optical camera, a light source of preferably at least one light-emitting diode (LED) (e.g., visible light), a scanning laser, and a second camera used to map the laser. In some embodiments, the scanning laser may be detected by the same optical camera in near to mid infrared imaging as optical sensor technology continues to advance. In its simplest form, as detailed below, the endoscope uses a typical arrangement of these components on the distal end of the endoscope. In order to reduce the required distal end diameter of the instrument and to improve triangulation between the laser and the second camera, these four components may have a location on at least one extensible surface. This enables the four components to be arranged along the side of the extensible surface such that the needed space for the individual components is provided by having a cross section equal or slightly larger than any single component and sufficient length to align the components side by side.

The computation of the topology viewed by the endoscope may require a calibration source to detail the alignment of the laser with the second camera. Anticipated is that the calibration may be conducted at the time of manufacture and stored within a memory coupled to a suitable computer, as will be described in detail hereinbelow, or by targeting a calibration surface at the time of use. The calibration will be used internally with the device anticipating the computational topology that may be created with the endoscope and transmitted for clinician via common video transmission means or the raw camera data along with the calibration may be transmitted to an external graphics processor creating the computational topology.

In some embodiments, at least the laser and the second camera may be spaced along the length of the instrument shaft to enable triangulation where the laser and second camera are directed at an angle from the centerline of the instrument.

One advantage of the disclosure is to enable three-dimensional surfacing of organs and other anatomical features and objects in a surgical site which can be matched to preoperative computational imaging needed for operative guidance to target lesions with particular special knowledge of adjacent structures and anatomic boundaries such as in sublobar resection or lung cancer. Primary use for this system is thoracic but one can vision equal value in deep pelvic, rectal surgery, or other surgical applications. These and further aspects of the disclosure are detailed herein below.

Figure 2:
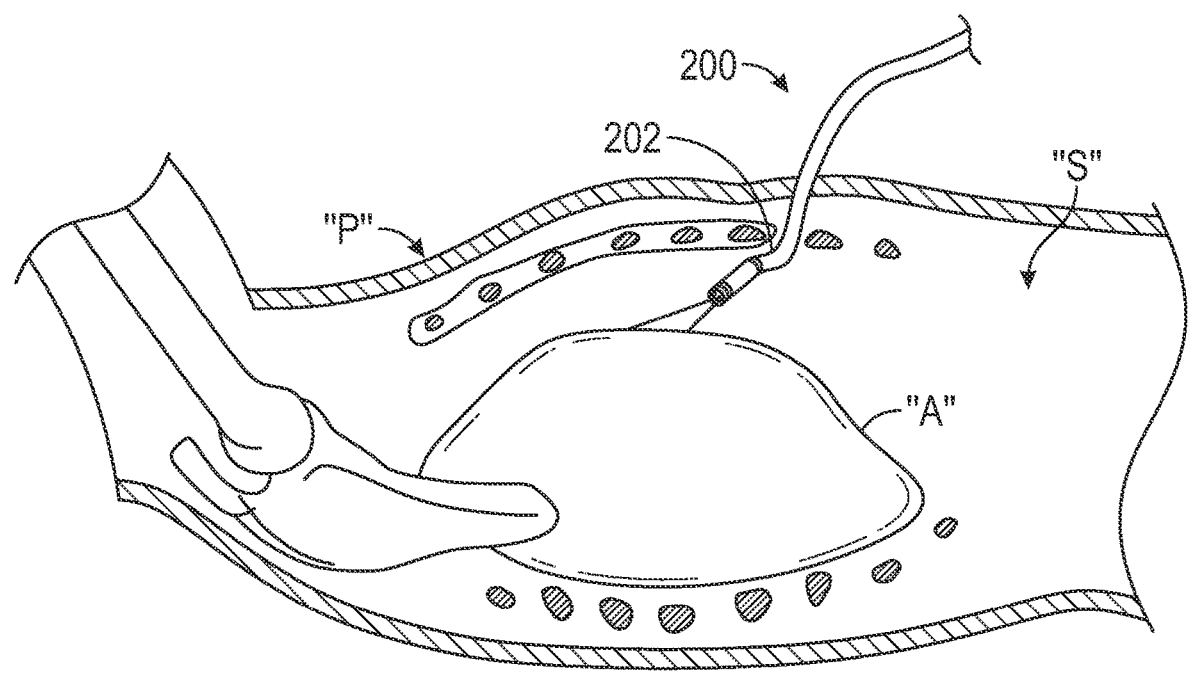
FIG. 2 is a side, cross-sectional, view of the thoracic cavity of a patient with the 3D endoscope of FIG. 1 advanced therein.
Figure 3:
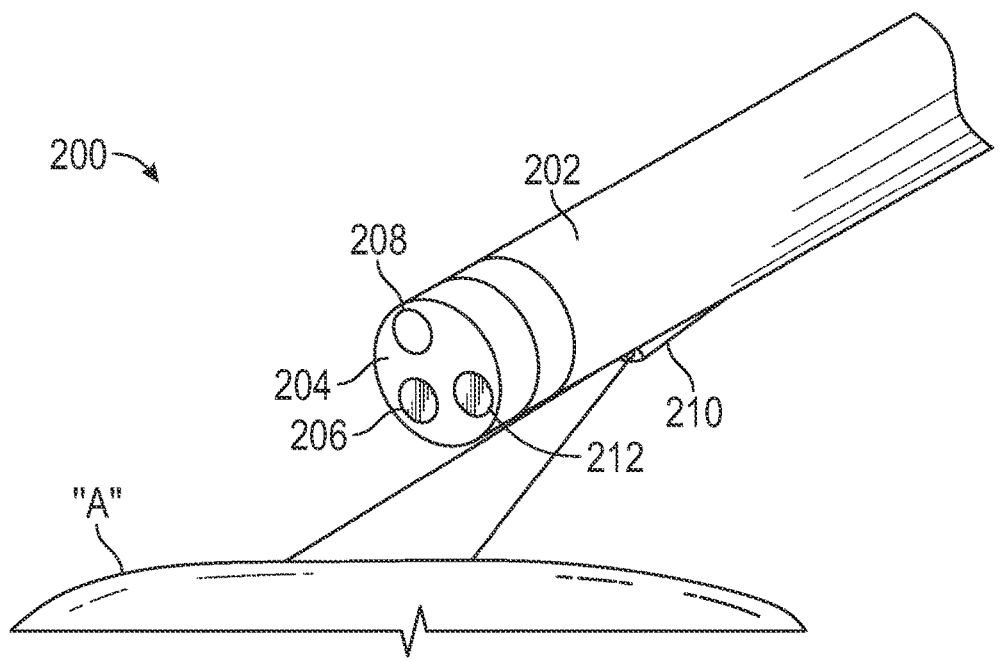
FIG. 3 is a front, perspective view, of a distal portion of the 3D endoscope of FIG. 1.

FIGS. 1-3 illustrate a system for enhanced surgical navigation in accordance with the disclosure, which is illustrated and generally described as system 100. System 100 includes a computing device 150 and a 3D endoscope configured to scan a surgical site "S" of a patient "P". The 3D endoscope is coupled to the computing device 150 and either the 3D endoscope or the computing device is configured to generate a 3D spatial map of the surgical site "S".

The 3D endoscope 200 includes an elongate body 202 configured to be advanced within a suitable thoracic trocar (not shown) or other device capable of penetrating the chest cavity and receiving an endoscope therein or a thoracic catheter or the like. In embodiments, the elongate body 202 may include segments capable of being manipulated relative to one another. In this manner, the 3D endoscope 200 may be positioned in close proximity to the chest wall to navigate the shallow portions of the surgical site "S" (e.g., the thoracic cavity) between the lungs or other anatomy "A" (FIG. 1) and chest wall of the patient "P". As can be appreciated, the elongate body 202 may include any number of segments to aid in the maneuverability of the 3D endoscope 200 within the surgical site "S" (e.g., the thoracic cavity).

FIG. 2 illustrates the distal portion of the 3D endoscope 200, which includes an optical camera 206, a light source 208, a structured light projection source or structured light scanner (laser) 210, and a second camera 212. It is contemplated that each of the optical camera 206, light source 208, laser 210, and second camera 212 may be disposed or coupled to 3D endoscope 200 in any suitable configuration. The optical camera 206 is a visual-light optical camera, such as a charge-coupled device (CCD), complementary metal-oxide-semiconductor (CMOS), N-type metal-oxide-semiconductor (NMOS), or other suitable camera known in the art. In one non-limiting embodiment, the optical camera 206 is a CCD camera having a resolution of 1080p. The light source 208 is a light emitting diode (LED) emitting white light, although any light emitting device known in the art may be utilized. The laser 210 may be any structured light scanner known in the art, such as an LED or LED infrared laser that is dispersed into a scan pattern (line, mesh, or dots), by rotating mirror, beam splitter, diffraction grating, or panning of the laser 210 itself. In one non-limiting embodiment, the laser 210 is an LED laser having collimated light. The second camera 212 is a CCD camera capable of detecting IR light, although it is contemplated that the second camera 212 may detect visible light, such as visible green light or the like, depending upon the tissue being scanned. Specifically, visible green light contrasts with tissue having a red or pinkish hue enabling the second camera 212 to more easily identify the topography of the tissue. A digital filter (not shown) or a filter having narrow band optical grating (not shown) inhibits extraneous visible light emitted from the laser 210 from distracting the surgeon during the surgical procedure. In embodiments, the visible light is filtered from the image captured by the optical camera 206 and transmitted to the surgeon such that the image is clear and free from extraneous light patterns.

It is contemplated that the second camera 212 may be any thermographic camera known in the art, such as such as ferroelectric, silicon microbolometer, or uncooled focal plane array (UFPA), or may be any other suitable visible light camera such as a charge-coupled device (CCD), complementary metal-oxide-semiconductor (CMOS), N-type metal-oxide-semiconductor (NMOS), or other suitable camera known in the art where the light emitted from the laser 210 is in the visible or detectable spectrum. In embodiments, the distal surface 204 may include a suitable transparent protective cover (not shown) capable of inhibiting fluids or other contaminants from coming into contact with each of the optical camera 206, light source 208, laser 210, and second camera 212. Since the distance between the laser 210 and second camera 212 relative to the optical camera 206 is fixed (i.e., the offset of the optical camera 206 relative to the laser 210 and second camera 212), the images obtained by the optical camera 206 can more accurately be matched with a pre-operative image, as will be described in further detail hereinbelow.

In operation, initially, the patient "P" (FIG. 1) is imaged using any suitable imaging device (not shown), such as MRI, ultrasound, CT scan, Positron Emission Tomography (PET), or the like, and the images are stored within a memory (not shown) coupled to computing device 150. The memory may include any non-transitory computer-readable storage media for storing data and/or software that is executable by a processor (not shown) e.g., solid-state, volatile, non-volatile, removable, and non-removable.

After the patient "P" is imaged, the clinician penetrates the chest of a patient "P" using a trocar (not shown) or other suitable device. The distal portion of the 3D endoscope 200 is advanced within the trocar, and thereafter, within the surgical site "S" (e.g., the thoracic cavity) of the patient "P" (FIG. 2). As the 3D endoscope 200 is further advanced within the thoracic cavity, the clinician observes the images obtained by the optical camera on a display (not shown).

Once facing the surface of the anatomy "A", for example the lung "L" (e.g., incident the lung surface), the laser 210 emits IR light, which is reflected off the surface of the anatomy "A" and detected by the second camera 212. The 3D endoscope 200 is advanced over the surface of the anatomy "A" in a caudal, cephalad, or lateral direction, or combinations thereof. The data obtained by the second camera 212 is processed by the computing device 150 to generate a 3D spatial map of the surface of the surgical site "S" including the anatomy "A" and any objects present therein, such as surgical tools, using any suitable means, such as stitching or the like. In an aspect, the clinician advances the 3D endoscope 200 over the entire surface of the anatomy "A" in order to obtain as complete a map as possible.

The light source 208 and the optical camera 206 are simultaneously operated with the laser 210 and second camera 212 to permit correlation of the images received from the optical camera 206 with the previously acquired MRI (or other modality identified above) images. The correlation between the images obtained by the optical camera 206 and the previously acquired MRI images permits the clinician, and the computing device 150, to more accurately map the surface of the anatomy "A" and the surgical site "S". As can be appreciated, the accuracy of the correlation may be further improved using tracking software to track the distal tip of the 3D endoscope 200.

Referring now to FIGS. 4, 5A-5C, 6, and 7A-7B, methods of enhanced surgical awareness during surgical navigation using system 100 and various graphical user interfaces are illustrated and will be described. Although the methods illustrated and described herein are illustrated and described as being in a particular order and requiring particular steps, any of the methods may include some or all of the steps and may be implemented in any order. Additionally, any or all of the steps of any of the methods described herein may be carried out by computing device 150 of system 100 or any other component or combination of components of system 100, including the 3D endoscope.

Figure 4:
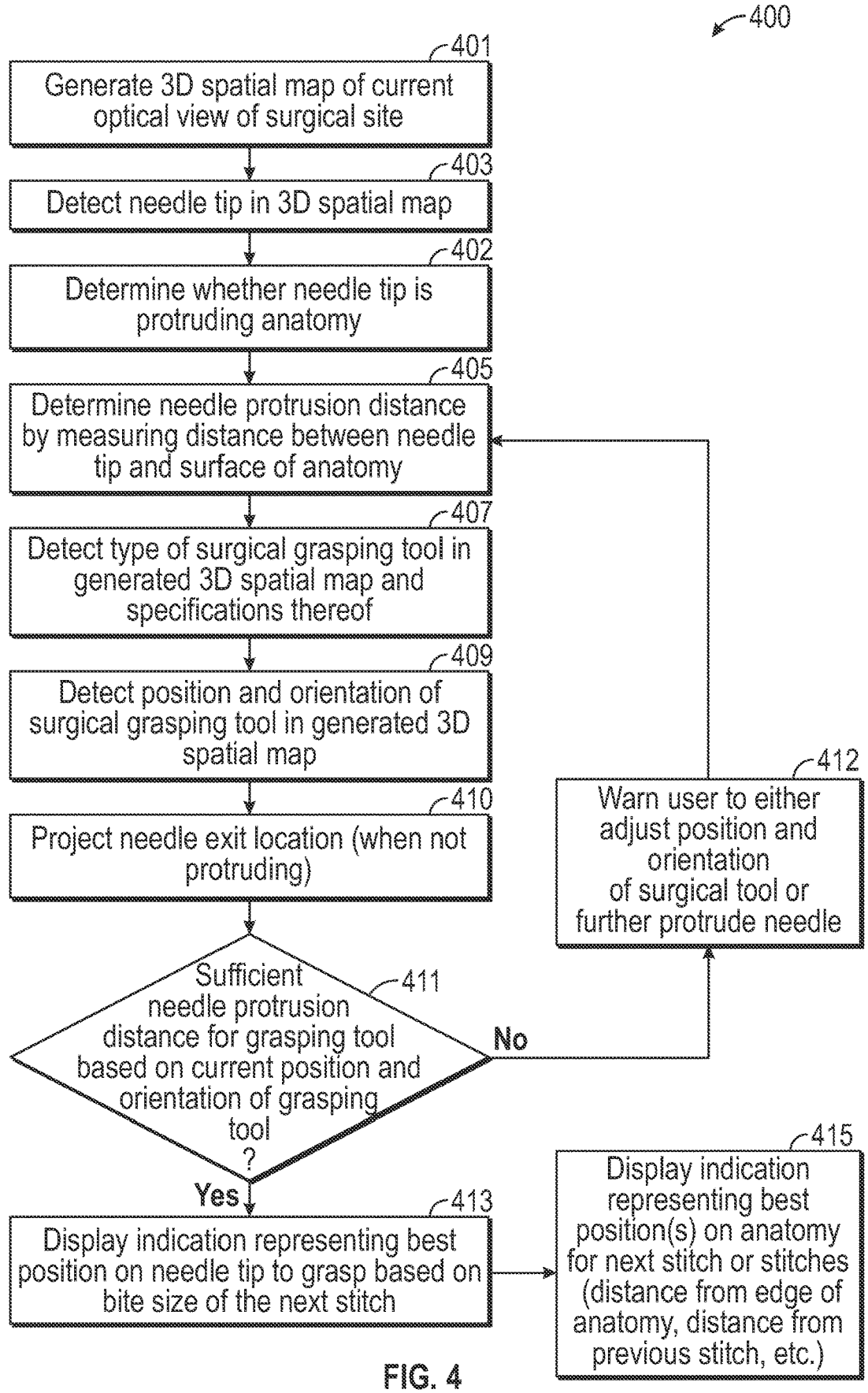
FIG. 4 is a flowchart illustrative of a method for enhancing surgical awareness and generating warnings and recommendations in accordance with an aspect of the disclosure.

FIG. 4 illustrates a flowchart of method 400, which is a method for enhanced surgical navigation that displays measured distances between a needle "N" tip and a surface of anatomy "A" through which the needle "N" protrudes, displays a recommended and optimal grasping point on the needle "N" for a user to grasp via the surgical tool "ST", warns a user when the position or orientation of the surgical tool "ST" is insufficient for grasping the needle "N" tip, and displays a recommended and optimal stitching point 509a on the anatomy "A".

Method 400 begins at step 401 where a 3D spatial map of a surgical site "S" is generated using a 3D endoscope described above. A view of the surgical site "S", including the anatomy "A" within the surgical site and any surgical tools present therein, as captured by the 3D endoscope is displayed in real time on a graphical user interface displayed on computing device 150.

Optionally, a selection of an anatomy "A" within the surgical site "S" is made. This selection may be carried out in real time using the images or data captured by the 3D endoscope or during a planning phase using images or data captured by some other imaging device such as a fluoroscope, CT, MRI, or PET scanner. For example, referring briefly to FIG. 5A, the selection of the anatomy "A" may be made by the user via graphical user interface 500a. Graphical user interface 500a includes a real time image 501a of the surgical site "S" as captured by 3D endoscope. A user may select the anatomy "A" in graphical user interface 500a within the real time image 501a or via a selection of the name of the anatomy "A" from a list of anatomical features (not shown) detected within the real time image 501a.

In step 402, a determination is made as to whether the needle tip of the needle is protruding from the anatomy. Various methods may be utilized to make this determination including, but not limited to, image analysis or spatial analysis using the aspects of the system described herein.

In step 403, the needle "N" tip is detected in the 3D spatial map. In step 405, the distance between the tip of the needle "N" and the surface of the anatomy "A" through which the needle "N" protrudes is determined (e.g., measured) using the data available in the 3D spatial map. In an aspect, the 3D spatial map includes a matrix of equidistant data points representing fixed points in a current view of the surgical site "S" and a value of a data point represents an existence of an object at the data point in space. For example, one object can be the tip of the needle "N" and another object can be the surface of the anatomy "A" selected or, in this case, the surface of the anatomy "A" through which the needle "N" protrudes. The distance between the detected position of the tip of the needle "N" in the 3D spatial map and the surface of the anatomy "A" in the 3D spatial map may be achieved by calculating a difference between coordinates of two data points (e.g., the point representing the tip of the needle "N" and the point representing the surface of the anatomy "A") in the matrix. Additionally, or alternatively, the distance between the detected position of the tip of the needle "N" in the 3D spatial map and the surface of the anatomy "A" in the 3D spatial map may be achieved by following a contour of a surface between two data points (e.g., the point representing the tip of the needle "N" and the point representing the surface of the anatomy "A") in the matrix and calculating a distance along the contour. This is particularly useful for curved needles or non-linear anatomical surfaces.

Following the measurement in step 405, in step 407, the type of surgical tool "ST" in the surgical site "S" is detected. This detection may be via a user input of the make and model of the surgical tool "ST" being used or via optical detection of the surgical tool "ST" within the 3D spatial map. The detection in step 407 may additionally include deriving the specifications of the surgical tool "ST", for example, the grasping strength, area, staple cartridge sizing, and other such details.

In step 409, the position and orientation of the surgical tool "ST", for example relative to the anatomy "A", in the generated 3D spatial map is determined. As described above with respect to the distance measurements (step 405), the position and orientation of the surgical tool "ST" relative to the anatomy "A" is determined (e.g., detected) using the data available in the 3D spatial map. In an aspect, the 3D spatial map includes a matrix of equidistant data points representing fixed points in a current view of the surgical site "S" and a value of a data point represents an existence of an object at the data point in space. For example, one object can be the surgical tool "ST" and another object can be the anatomy "A". The position and orientation of the surgical tool "ST" in the 3D spatial map relative to the anatomy "A" in the 3D spatial map may be achieved by calculating a difference between coordinates of two data points (e.g., the point representing the surgical tool "ST" and the point representing the anatomy "A") in the matrix. Additionally, or alternatively, the position and orientation of the surgical tool "ST" in the 3D spatial map relative to the anatomy "A" in the 3D spatial map may be achieved by following a contour of a surface between two data points (e.g., the point representing surgical tool "ST" and the point representing the anatomy "A") in the matrix, calculating a distance along the contour, and deriving the position and orientation therefrom.

Figure 5A:
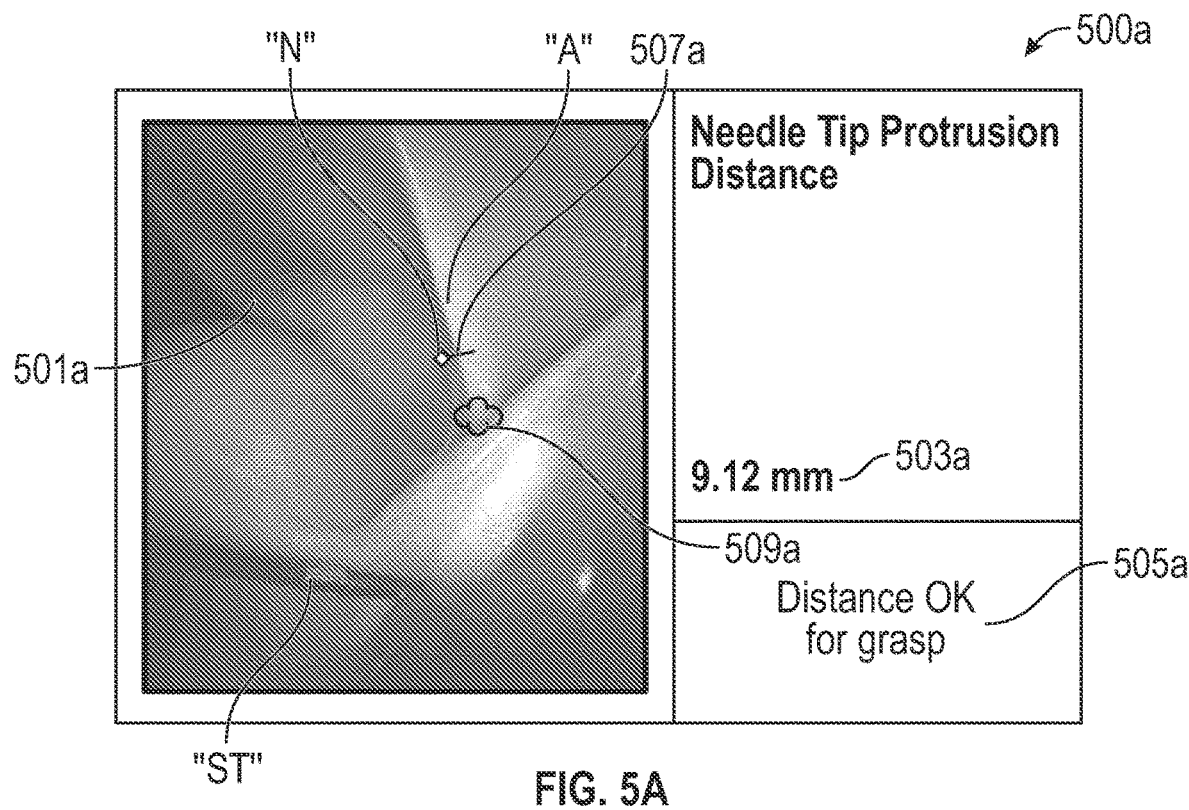
FIG. 5A is an exemplary graphical user interface displaying a value representing a measured distance between a needle tip and a surface of an anatomy and a recommended position for grasping the needle tip in accordance with the method of FIG. 4.
Figure 5B:
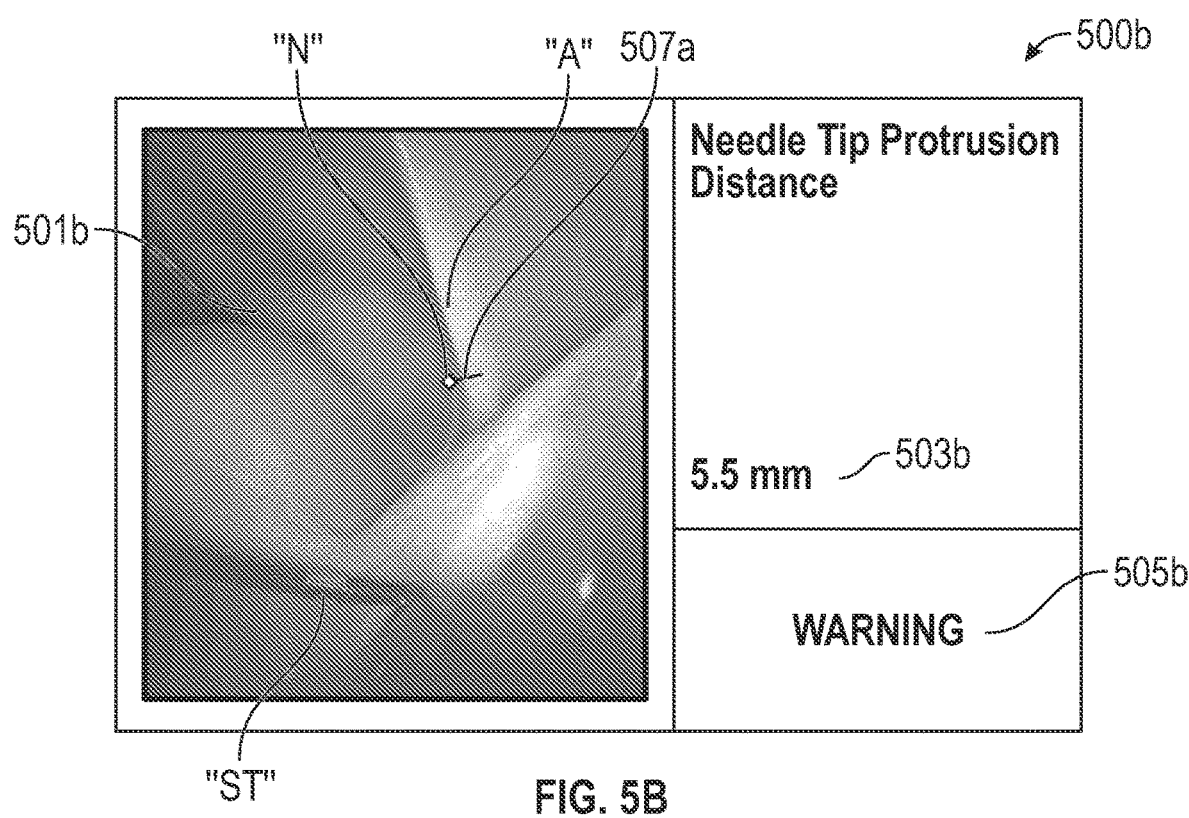
FIG. 5B is an exemplary graphical user interface displaying a value representing a measured distance between a needle tip and a surface of an anatomy and a warning message in accordance with the method of FIG. 4.
Figure 5C:
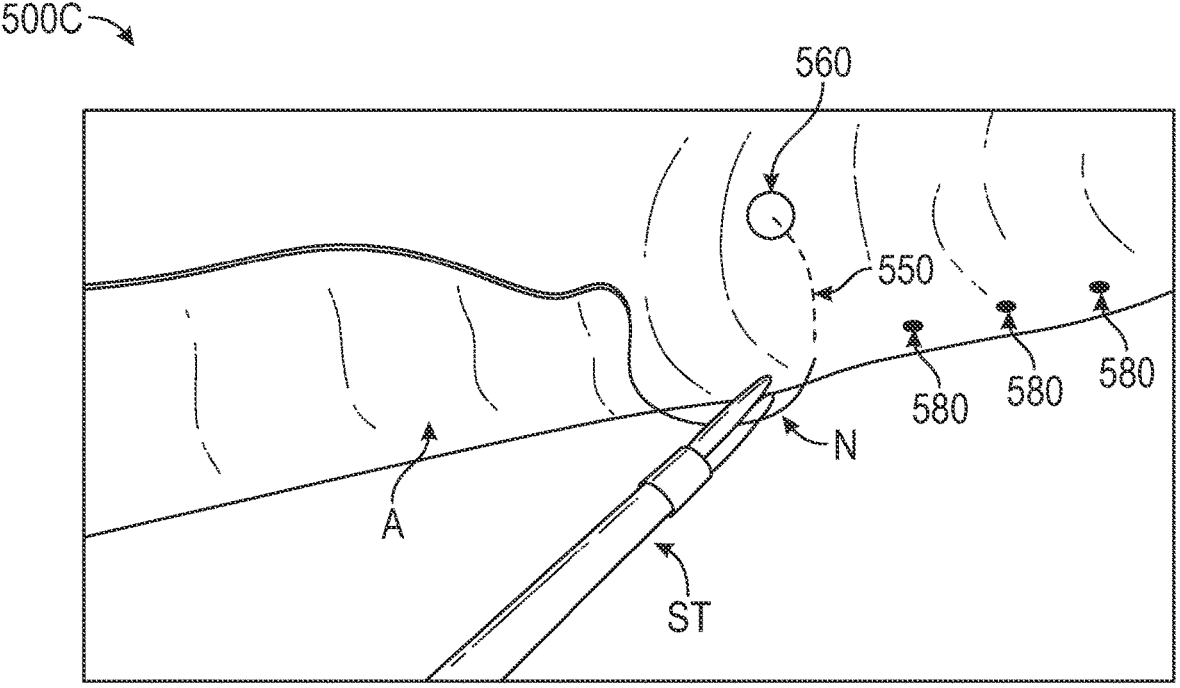
FIG. 5C is an exemplary graphical user interface displaying a projected needle path, projected exit location, and subsequent stitch locations in accordance with an aspect of the disclosure.

In step 410, the projected needle path through the anatomy and the projected needle exit location are calculated based on the current position of the needle. The projected needle path and projected needle exit location are calculated in real time based on the current position and orientation of the needle when it is determined that the needle tip is not protruding the anatomy (no in step 402). Such data may be useful for displaying or identifying possible or potential intersection with a critical structure or to show where the needle will come out of the anatomy relative to a desired location (which may also be displayed). In making this calculation, the system may consider many factors including, but not limited to, the orientation, position, length, and curve of the needle, where such factors are detected by the system or input by a user. FIG. 5C illustrates an exemplary user interface 500C which shows the projected needle path 550 of the needle "N" through the anatomy "A" along with the projected needle exit location 560 made available to a user for viewing. Although not shown in FIG. 5C, a desired needle exit location may also be displayed for comparison to the calculated/displayed needle exit location. The data of such calculations made for display are also usable by robotic systems for controlling the surgical tool "ST" and for calculating and displaying subsequent needle stitch points 580 (described in further detail below).

In step 411, a determination is made as to whether or not there exists sufficient grasping area on the exposed portion of the needle for grasping by the surgical tool "ST" based on the current position and orientation of the surgical tool "ST" (detected in step 409) and the determined needle protrusion distance (detected in step 405). If there does not exist sufficient grasping area on the exposed portion of the needle "N" for grasping by the surgical tool "ST" (no in step 411), then method 400 proceeds to step 412, where the system 100 notifies the user to either adjust the position and orientation of the surgical tool "ST" in the surgical site or to further protrude the needle "N" if possible. Such a display is illustrated in the graphical user interface 500b shown in FIG. 5B, which includes a real time image 501b of the surgical site "S", the current real time position of the surgical tool "ST", the selected anatomy "A", a value 503b representing the measured distance between the tip of the needle "N" and the surface of the anatomy "A", and a notification 505b. The notification 505b, although shown as a visual notification on a graphical user interface 500b, may additionally or alternatively include, visual, audible, tactile feedback, or any combinations thereof. In an aspect, the notification is in the form of modifying or displaying the value 503b in an abnormal form to draw attention to the user that sufficient grasping area does not currently exist.

On the other hand, if there does exist sufficient grasping area on the exposed portion of the needle "N" for grasping by the surgical tool "ST" (yes in step 411), then method 400 proceeds to step 413, where the system 100 displays the best position on the needle "N" for the surgical tool "ST" to grasp the needle "N". In step 415, for suture applications, an indication is displayed on the anatomy "A" which represents the best position for the next stitch based on the type of anatomy "A", the type of stitch, the distance from the edge of the anatomy "A", the distance from the previous stitch, or any combination of these factors. This may include the starting point for all remaining stitches (as seen in FIG. 5C). For example, such a display is illustrated in the graphical user interface 500a shown in FIG. 5A, which includes a real time image 501a of the surgical site "S", the current real time position of the surgical tool "ST", the selected anatomy "A", a value 503a of the measured distance of the tip of the needle "N" protruding from the anatomy "A", the best point on the needle "N" for grasping 507a, and the best position 509a on the anatomy "A" for the next stich. Additionally, shown in the graphical user interface 500a, is a notification 505a indicating that sufficient grasping area exists on the exposed portion of the needle "N" for grasping by the surgical tool "ST". In an aspect, the notification 505a may include displaying the value 503a in a normal form.

Figure 6:
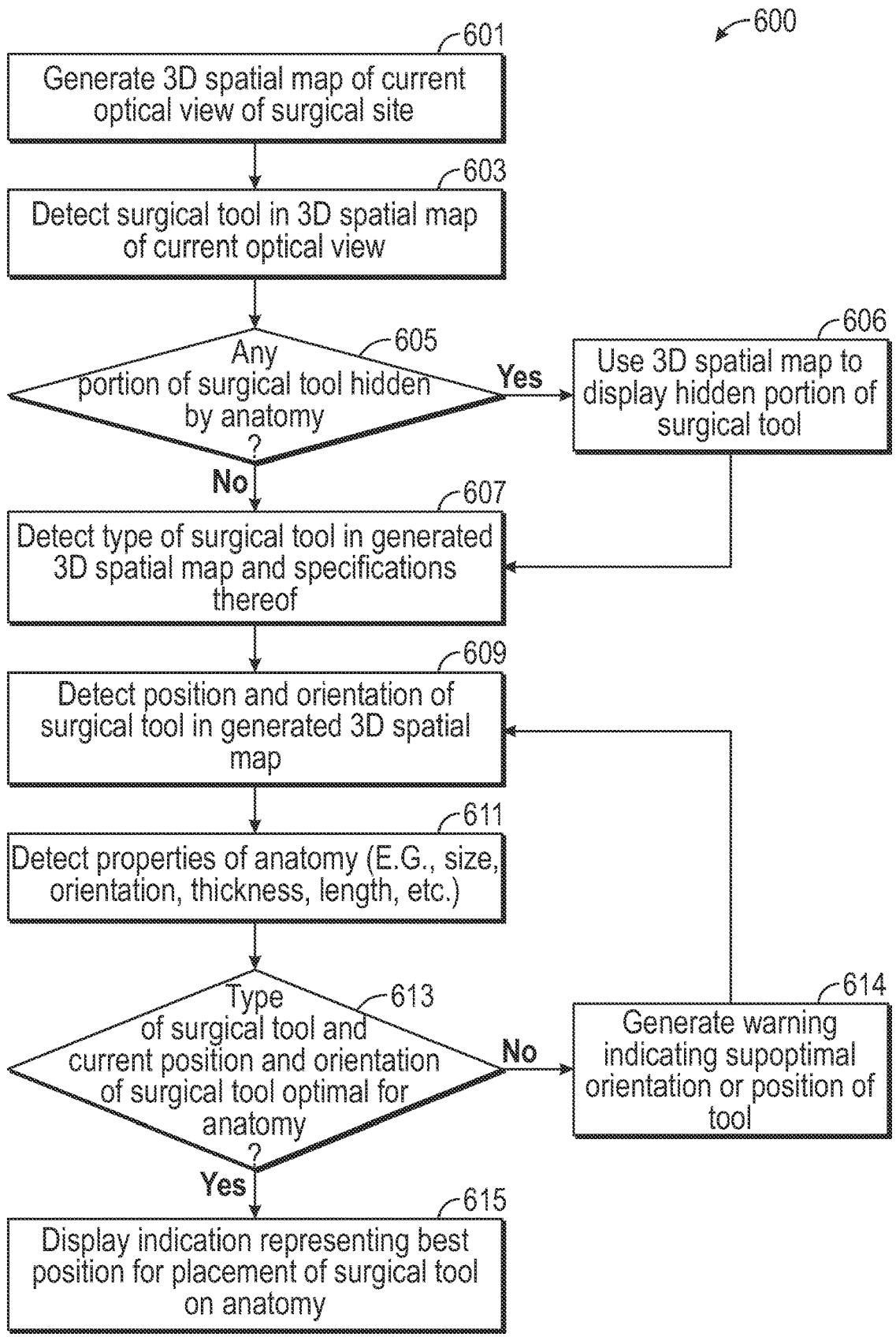
FIG. 6 is a flowchart illustrative of a method for enhancing surgical awareness and generating warnings and recommendations in accordance with an aspect of the disclosure.

FIG. 6 illustrates a flowchart of method 600, which is a method for enhanced surgical navigation that displays portions of the surgical tool "ST" that are hidden (e.g., behind) portions of the anatomy "A" or other structures within the surgical site "S". Method 600 begins at step 601 where a 3D spatial map of a surgical site "S" is generated using a 3D endoscope described above. A view of the surgical site "S", including the anatomy "A" within the surgical site "S" and any surgical tools present therein, as captured by the 3D endoscope is displayed in real time on a graphical user interface displayed on computing device 150.

In step 603, the surgical tool "ST" is detected in the current optical view of the 3D spatial map. In step 605, a determination is made as to whether any portion of the surgical tool "ST" is not visible within the current optical view. For example, it may be determined that a portion of the surgical tool "ST" is hidden behind an object such as the anatomy "A" or any other structures or anatomical features within the surgical site "S".

Figure 7A:
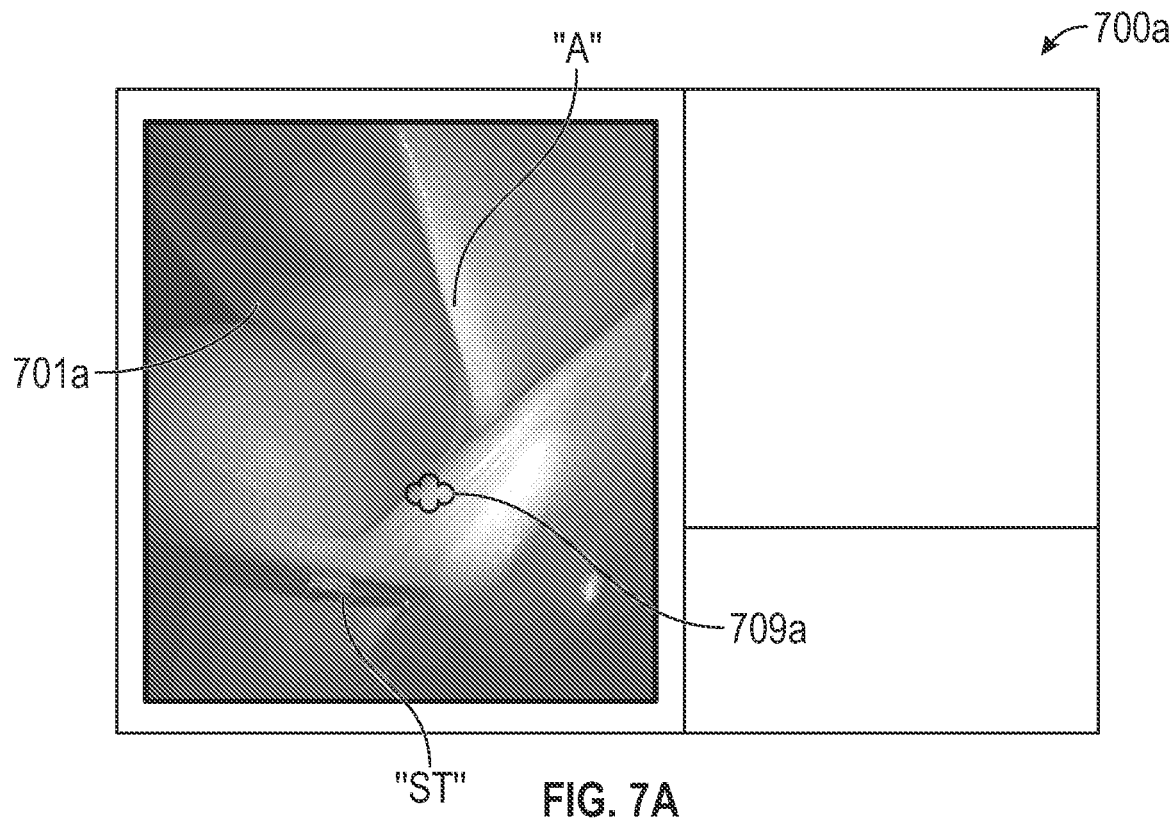
FIG. 7A is an exemplary graphical user interface displaying a surgical tool and a recommended position for contacting an anatomy in accordance with the method of FIG. 6.
Figure 7B:
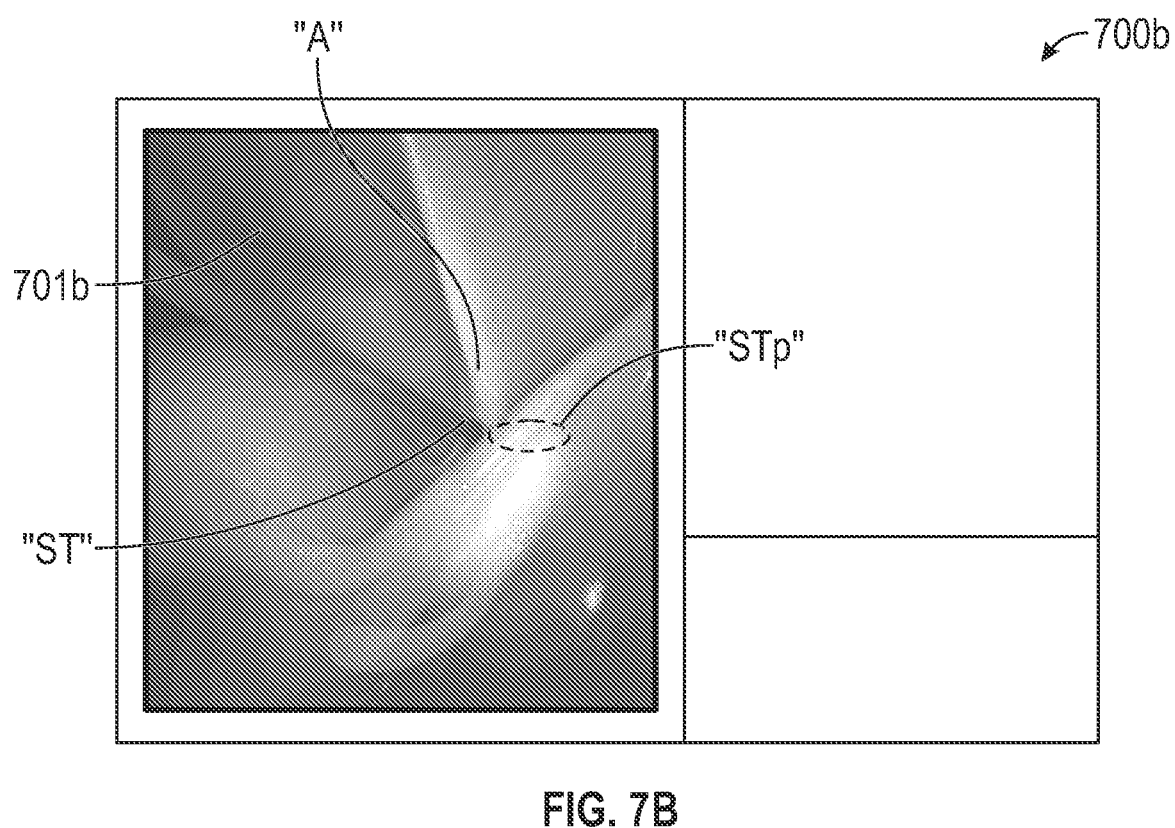
FIG. 7B is an exemplary graphical user interface displaying a surgical tool and a phantom of the surgical tool that is hidden behind an anatomy in accordance with the method of FIG. 6.

If it is determined that any portion of the surgical tool "ST" is hidden (yes in step 605), then method 600 proceeds to step 606, where the 3D spatial map is utilized to display a hidden portion of the surgical tool "ST". For example, the hidden portion of the surgical tool "ST" may be displayed in phantom behind the object that is hiding it. An exemplary graphical user interface illustrating such a feature is shown in FIG. 7B. In particular, referring to FIG. 7B, a graphical user interface 700b includes a current optical view of the surgical site "S" including the surgical tool "ST", the anatomy "A", and the portion of the surgical tool "ST" that is hidden by the anatomy "A" in phantom "STp". Following step 606, method 600 proceeds to step 607 as described below.

On the other hand, if it is determined that no portion of the surgical tool "ST" is hidden in the current optical view (no in step 605), then method 600 proceeds to step 607. In step 607, the type of surgical tool "ST" in the surgical site "S" is detected. This detection may be via a user input of the make and model of the surgical tool "ST" being used or via optical detection of the surgical tool "ST" within the 3D spatial map. The detection in step 607 may additionally include deriving the specifications of the surgical tool "ST", for example, the grasping strength, area, staple cartridge sizing, and other such details.

In step 609, the position and orientation of the surgical tool "ST", for example relative to the anatomy "A" in the generated 3D spatial map is determined. As described above with respect to the distance measurements (step 405 of method 400), the position and orientation of the surgical tool "ST" relative to the anatomy "A" is determined (e.g., detected) using the data available in the 3D spatial map. In an aspect, the 3D spatial map includes a matrix of equidistant data points representing fixed points in a current view of the surgical site "S" and a value of a data point represents an existence of an object at the data point in space. For example, one object can be the surgical tool "ST" and another object can be the anatomy "A". The position and orientation of the surgical tool "ST" in the 3D spatial map relative to the anatomy "A" in the 3D spatial map may be achieved by calculating a difference between coordinates of two data points (e.g., the point representing the surgical tool "ST" and the point representing the anatomy "A") in the matrix. Additionally, or alternatively, the position and orientation of the surgical tool "ST" in the 3D spatial map relative to the anatomy "A" in the 3D spatial map may be achieved by following a contour of a surface between two data points (e.g., the point representing surgical tool "ST" and the point representing the anatomy "A") in the matrix, calculating a distance along the contour, and deriving the position and orientation therefrom.

In step 611, system 100 detects the properties of the anatomy "A". For example, such properties may include the size, orientation in the current optical view or relative to the current position of the surgical tool "ST", thickness, length, or other properties. Such properties of the anatomy "A" may be derived via the data available from the 3D spatial map.

In step 613, system 100 determines if the type of surgical tool "ST" (detected in step 607) and the current position and orientation of the surgical tool "ST" relative to the anatomy "A" (detected in step 609) is optimal for the anatomy "A", based on the properties of the anatomy (detected in step 611). If system 100 determines that either the type or current position and orientation are not optimal for the anatomy "ST" (no in step 613), then method 600 proceeds to step 614, where a warning is generated. Such a warning may include notifying the user to reorient or reposition the surgical tool "ST".

On the other hand, if system 100 determines that the current position and orientation of the surgical tool "ST" are optimal for the anatomy "A" (yes in step 613), then method 600 proceeds to step 615, where an indication representing the best position for placement of the surgical tool "ST" on the anatomy "A" is displayed. For example, referring to FIG. 7A, a graphical user interface 700a is shown including a current view 701a of the surgical site "S", the surgical tool "ST", the anatomy "A", and an indication 709a representing the best position for contacting (e.g., placing, grasping, etc.) the anatomy "A".

In addition to the above-described methods performable by system 100, system 100 may detect coordinate mismatches and notify the user or modify the display of the graphical user interface based on the detected mismatch. The anatomy being scanned is not static and will change over time due to elements such as manipulation by the surgeon, natural biological rhythms (e.g. cardiac, pulmonary), and gravity. Detection of such changes by system 100 can include three-dimensional coordinate mismatches between current scanned locations of objects in the current field of view and those from a previous view (e.g. a surface that extends out of the current view where the Y coordinates of the surface in view differs from that outside). Previously scanned structures completely outside of the current view may change as well. In an aspect, system 100 indicates to the user that all items outside the current field of view may have changed. To this end, system 100 may modify the displayed image of all elements outside the current field of view via blurring, removing three-dimensional effects (e.g., flattening the image), and removal of color or fading of color. Each technique can have subtleties such as keying the extent of the effect to the age of the image since it was last refreshed.

Surgical instruments such as the endoscopes, computing devices, and other components of system 100 described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, endoscopes, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

It is contemplated that the endoscopes and aspects (e.g., components) of the system described herein may be positioned by the robotic system, the data calculated by the system may be used to control components of the robotic system, and the precise position of the endoscope transmitted to the computer to construct the 3D image of the scanned organ or operative field. The robotic system has the ability to autonomously scan the surgical field and construct a complete 3D model of the field to aid the surgeon in directing the robotic arms or to provide necessary 3D information for the robotic system to further conduct surgical steps autonomously. In embodiments, where the endoscope includes a camera and a structured light source that are independent of one another, the robotic system may direct the camera and a structured light source separately. The robotic system provides the relative coordinates between respective endoscopes needed to triangulate the points in the structured light and camera views to construct a 3D surface of the operative field. In this manner, the robotic system has a specific advantage of being able to autonomously position the structure light source onto the field of view of the camera or camera endoscope.

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
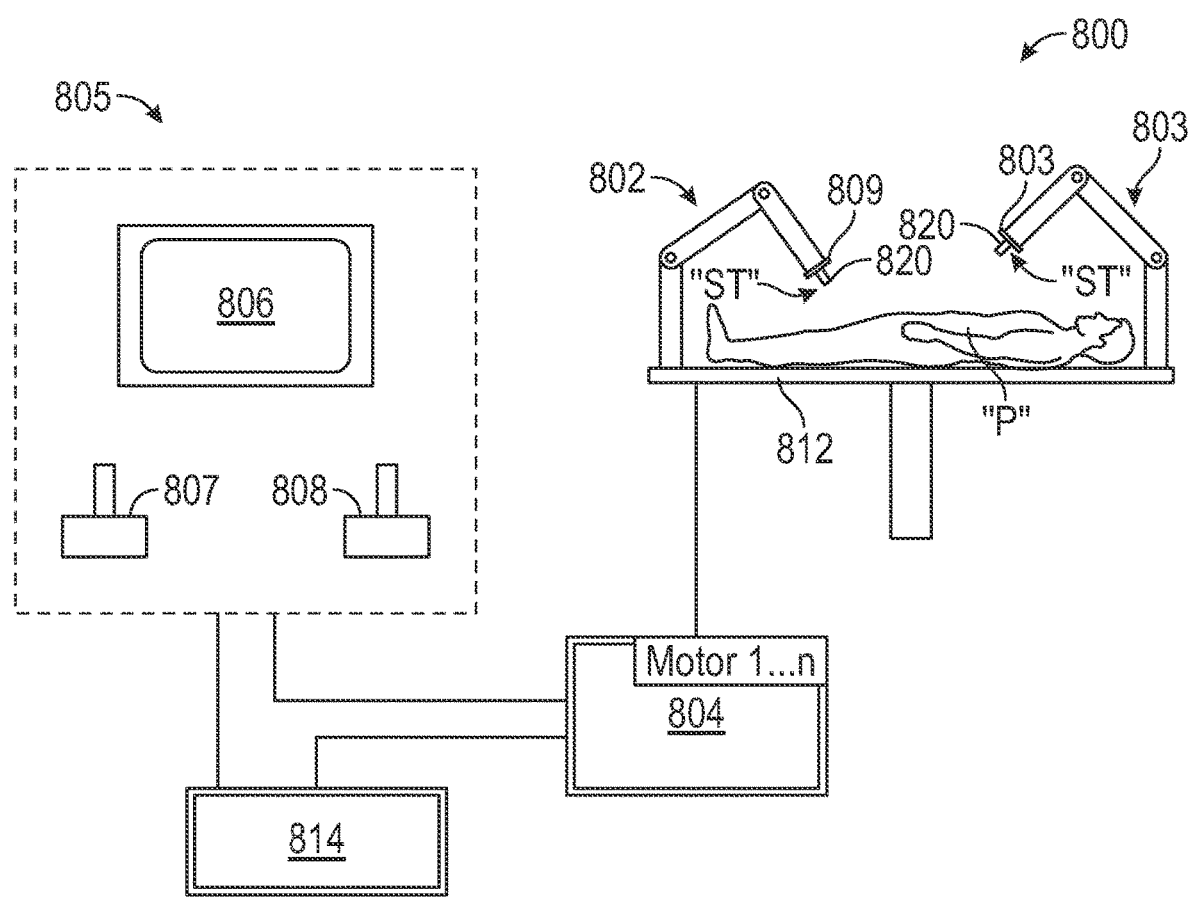
FIG. 8 is a schematic illustration of a robotic surgical system configured for use in accordance with the disclosure.

FIG. 8 illustrates a medical work station, shown generally as work station 800 and generally may include a plurality of robot arms 802, 803, a control device 804, and an operating console 805 coupled with control device 804. Operating console 805 may include a display device 806, which may be set up in particular to display three-dimensional images, and manual input devices 807, 808, by means of which a person (not shown), for example a surgeon, may be able to telemanipulate robot arms 802, 803 in a first operating mode.

Each of the robot arms 802, 803 may include a plurality of members, which are connected through joints, and an attaching device 809, 811, to which may be attached, for example, a surgical tool "ST" supporting an end effector 820, in accordance with any one of several embodiments disclosed herein, as will be described in greater detail below.

Robot arms 802, 803 may be driven by electric drives (not shown) that are connected to control device 804. Control device 804 (e.g., a computer) may be set up to activate the drives, in particular by means of a computer program, in such a way that robot arms 802, 803, their attaching devices 809, 811 and thus the surgical tool (including end effector 820) execute a desired movement according to a movement defined by means of manual input devices 807, 808. Control device 804 may also be set up in such a way that it regulates the movement of robot arms 802, 803 and/or of the drives. Movement of robot arms 802, 803 may be constrained to specific motions or ranges of motion based on the 3D model created by the endoscope and system described herein or other calculations made by the system described herein. In addition, and for example, the calculations made by the system may be used to control the robot arms 802, 803 in such a manner as to enable a robot arm 802, 803 to grasp the correct point of the needle. Where insufficient area of the needle is available for grasping (as calculated), the robotic system may control any of robot arms 802, 803 to adjust the position of the needle until sufficient grasping area is made available. Additionally, the system may utilize the calculations corresponding to the distance measurements to the next or subsequent stitches to determine which of robot arms 803, 803 should be utilized the grasp the needle and/or make the next stitch.

Medical work station 800 may be configured for use on a patient "P" lying on a patient table 812 to be treated in a minimally invasive manner by means of end effector 820. Medical work station 800 may also include more than two robot arms 802, 803, the additional robot arms likewise being connected to control device 804 and being telemanipulatable by means of operating console 805. A medical instrument or surgical tool (including an end effector 1120) may also be attached to the additional robot arm. Medical work station 800 may include a database 814, in particular coupled to with control device 804, in which are stored, for example, pre-operative data from patient/living being "P" and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

As used hereinabove, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. Additionally, in the drawings and in the description above, terms such as front, rear, upper, lower, top, bottom, and similar directional terms are used simply for convenience of description and are not intended to limit the disclosure. In the description hereinabove, well-known functions or constructions are not described in detail to avoid obscuring the disclosure in unnecessary detail.

What is claimed is:

1. A method for enhanced surgical navigation, comprising:
    generating a 3D spatial map of a surgical site using a 3D endoscope, the 3D endoscope including a camera source and an IR scan source;
    detecting whether a needle tip of a needle is protruding from an anatomy in the 3D spatial map;
    determining a needle protrusion distance by measuring a distance between the needle tip and a surface of the anatomy using the 3D spatial map when the needle tip is protruding from the anatomy;
    detecting a position of a surgical tool in the 3D spatial map;
    generating a warning when it is determined that the needle protrusion distance is not sufficient for grasping by the surgical tool based on a current orientation of the needle when the needle tip is not protruding from the anatomy; and
    displaying an indication representing a best position on the needle tip protruding from the anatomy to grasp with the surgical tool.

2. The method of claim 1, further comprising displaying an indication representing a best position on the anatomy for a subsequent stitch based on at least one of a distance from an edge of the anatomy, a thickness of the anatomy, a distance from a previous stitch, or any combinations thereof.

3. The method of claim 1, wherein generating the warning includes notifying a user to further protrude the needle or to adjust the position of the surgical tool.

4. The method of claim 1, further comprising detecting a type of the surgical tool in the 3D spatial map and wherein determining whether the needle protrusion distance is sufficient for grasping by the surgical tool is based on the detected position of the surgical tool and the detected type of surgical tool.

5. The method of claim 1, further comprising:
    displaying a value representing the needle protrusion distance, and
    wherein generating the warning includes modifying the display of the value representing the needle protrusion distance.

6. The method of claim 1, wherein the 3D spatial map includes a matrix of equidistant data points representing fixed points in a current view of the surgical site and a value of a data point represents an existence of an object at the data point in space.

7. The method of claim 1, wherein determining the needle protrusion distance includes at least one of:
    calculating a difference between coordinates of two data points in the matrix; or
    following a contour of a surface between two data points in the matrix and calculating a distance along the contour.

8. The method of claim 1, further comprising:
    determining whether a portion of the surgical tool is hidden by an object in the surgical site; and
    using data from the 3D spatial map, displaying a hidden portion of the surgical tool when it is determined that a portion of the surgical tool is hidden by an object in the surgical site.

9. The method of claim 1, further comprising:
    detecting properties of the anatomy;
    determining whether the position of the surgical tool is optimal for grasping the anatomy based on the detected properties of the anatomy; and
    generating a warning when it is determined that the position of the surgical tool is not optimal for grasping the anatomy.

10. The method of claim 9, further comprising displaying an indication of a position on the anatomy for grasping the anatomy when it is determined that the position of the surgical tool is optimal for grasping the anatomy.

11. The method of claim 1, further comprising determining whether the needle protrusion distance is sufficient for grasping by the surgical tool based on the detected position of the surgical tool.

12. The method of claim 1, further comprising projecting a needle exit location based on a current orientation of the needle when the needle tip is not protruding from the anatomy.

* * * * *